United States Patent
Thilly (10) Patent No.: US 7,252,308 B2
(45) Date of Patent: Aug. 7, 2007

(54) CONNECTOR DEVICE FOR THE STERILE CONNECTION OF TUBES

(75) Inventor: Jacques Thilly, Rixensart (BE)

(73) Assignee: GlaxoSmithKline Biologicals s.a., Rixensart (BE)

( * ) Notice: Subject to any disclaimer, the term of this patent is extended or adjusted under 35 U.S.C. 154(b) by 313 days.

(21) Appl. No.: 10/495,398

(22) PCT Filed: Nov. 12, 2002

(86) PCT No.: PCT/EP02/12657

§ 371 (c)(1),
(2), (4) Date: Sep. 22, 2004

(87) PCT Pub. No.: WO03/041789

PCT Pub. Date: May 22, 2003

(65) Prior Publication Data

US 2005/0017505 A1 Jan. 27, 2005

(30) Foreign Application Priority Data

Nov. 13, 2001 (GB) ................................ 0127224.4

(51) Int. Cl.
*F16L 35/00* (2006.01)
*F16L 37/00* (2006.01)
(52) U.S. Cl. ........................ 285/3; 604/403; 604/905

(58) Field of Classification Search ................. 285/3; 137/614.04; 604/111, 171, 200, 244, 246, 604/263, 403, 905; D24/129; 141/25
See application file for complete search history.

(56) References Cited

U.S. PATENT DOCUMENTS

| 4,004,586 | A | * | 1/1977 | Christensen et al. ......... 604/413 |
| 4,019,512 | A | * | 4/1977 | Tenczar ....................... 604/411 |
| 4,022,205 | A | * | 5/1977 | Tenczar ....................... 604/411 |
| 4,030,494 | A | * | 6/1977 | Tenczar ....................... 604/411 |
| 4,187,846 | A | * | 2/1980 | Lolachi et al. .............. 604/411 |
| 4,610,469 | A | * | 9/1986 | Wolff-Mooij ............... 285/260 |
| 4,946,455 | A | * | 8/1990 | Rosen ......................... 604/403 |
| 5,810,398 | A | * | 9/1998 | Matkovich ..................... 285/3 |

FOREIGN PATENT DOCUMENTS

| EP | 0126650 | 11/1984 |
| GB | 2060399 | 5/1981 |

* cited by examiner

*Primary Examiner*—Aaron Dunwoody
*Assistant Examiner*—Fannie C. Kee
(74) *Attorney, Agent, or Firm*—Eric J. Kron (57) ABSTRACT

A connector for forming a sterile connection between two tubes, comprising first and second parts which comprise connectable conduits and which can mate, first and second covers which can be removed from the so-mated parts to expose connectable ends of the first and second conduits, so that the conduits can then be connected.

18 Claims, 7 Drawing Sheets

CONNECTOR DEVICE FOR THE STERILE CONNECTION OF TUBES

CROSS REFERENCE TO RELATED APPLICATIONS

This is a national stage application under 35 U.S.C. Section 371 of PCT application PCT/PCT/EP02/12657, filed on 22 Sep. 2004, which claims the benefit of GB0127224.4, filed on 13 Nov. 2001.

FIELD OF THE INVENTION

This invention relates generally to a connector device suitable for connecting two conduits.

BACKGROUND

A connection device for sterile connection of tubes is often required in situations where, for example, pharmaceutical substances such as vaccines etc. are manipulated and transferred via such conduits from one container or another type of enclosure to another. Such a connector is disclosed in U.S. Pat. No. 6,341,902 but in practice the connector disclosed therein can only connect small diameter tubing.

SUMMARY OF THE INVENTION

In one aspect is provided a means by which two such conduits may be connected whilst maintaining sterility. Other aspects will be apparent from the following description.

In one aspect is provided a connector for connecting two conduits that comprises, a first connector part and a second connector part which can mate together to form an enclosure between them bounded by a sterile seal, the first connector part and second connector part having respective first and second conduits passing through them, the conduits being relatively moveable within the enclosure formed on mating of the first and second connector parts to form a mating connection between the first and second conduits, in the unmated state of the first and second connector parts the first and second conduits being covered by respective first and second removable covers which can mate with each other and which form respective seals with the respective first and second connector parts to isolate the ends of the conduits from the ambient environment, configured such that on mating of the first and second connector parts the first and second removable covers also mate and form a sterile seal between them, and the mated covers may be separated from the respective first and second parts and received within the enclosure, to allow the conduits to relatively move and come into mating connection within the enclosure.

In one aspect there is a sterile seal between the first connector part and first removable cover; a sterile seal between the second connector part and second removable cover; a sterile seal between the first connector part and second connector part when mated; and a sterile seal between the first removable cover and the second removable cover when mated, and all of these seals meet at a common seal line. In one embodiment, this common seal line is the line at which the mated first and second removable covers are separated from the respective first and second parts.

An embodiment of the connector comprises;

a first connector part having a first sealing surface through which passes a first conduit having a first open end on one side of the sealing surface, a first removable cover engageable with the first connector part and which when so engaged forms a first seal between the first cover and the first part, and together with the first connector part forms a first enclosure enclosing the first open end, a second connector part defining at least part of a second enclosure, and having a second sealing surface which can be sealingly mated with the first sealing surface to form a second seal between these surfaces, an opening through the second sealing surface, a second removable cover engageable with the second connector part which when in place closes the opening at a third seal, and which together with the second connector part forms a second enclosure within the second connector part, and the second removable cover can mate with the first removable cover, a second conduit terminating in a second open end within the second enclosure and having an open end outside the second enclosure, wherein in operation the first and second parts mate to form the second seal between the first and second sealing surfaces, when so mated the first and second covers mate to form a fourth seal between the first and second covers, and the mated first and second covers enclosing between them parts of the first and second covers that before mating were exposed to the ambient environment, the mated first and second covers are detached from the mated first and second parts to expose the first and second ends respectively of the first and second conduits to each other, the first and second ends respectively of the first and second conduits are moveable relatively toward each other, and are moved relative to each other into communication, and wherein, the first, second, third and fourth seals meet along a common seal line, and the mated first and second covers detach from the mated first and second parts at this seal line.

In one aspect the first and second sealing surfaces comprise correspondingly shaped flange surfaces which meet in operation to form a sterile first seal between the first and second parts. The first and/or second sealing surfaces may comprise a compression seal, e.g. comprising a compressible elastomeric seal e.g. a washer, which compresses against a mating part of the second or first sealing surface. In one aspect the first and second parts have mating parts such as co-operating screw threads to facilitate their mating together.

In one aspect the first and second conduits are tubes, and the respective first and second ends are mating ends which can mate to form a fluid-tight communication, for example they may be male and female mating ends.

In one aspect the first removable cover can fit over the first open end of the first conduit, and the first part and first cover can have mating parts such as co-operating screw threads to facilitate the sealing of the cover against the first part. In one aspect a compression seal, e.g. a compressible elastomeric washer, is provided between the first cover and the first part when the cover is in place to facilitate a sterile seal. For example a part of the first connector part adjacent to the first open end of the conduit may be a concave surface defining at least part of the first enclosure, and the first removable cover may comprise a convex facing surface defining another part of the first enclosure.

In one aspect the second removable cover and the opening through the second connector part are provided with mating parts such as screw threads to facilitate the sealing of the cover against the second part to seal the opening.

In one aspect a compression seal, e.g. a compressible elastomeric washer, is provided between the second cover and the second part when the cover is in place to facilitate a sterile seal.

In one aspect the second removable cover may be detached from the second connector part by a movement inwardly into the second enclosure. In one embodiment, the second removable cover is completely detachable from the part of the second connector part that comprises the perimeter of the opening.

In one aspect the first and second covers are provided with mating parts such as respective co-operating screw threads to facilitate their mating together.

In one aspect the fourth seal between the first and second removable covers is facilitated by a compression seal between them, for example a compressible elastomeric washer.

In one aspect the mated first and second covers are detachable from the mated first and second parts by unscrewing of the second cover from the second part.

In one aspect the so-detached mated covers are received within the second enclosure, i.e. within the second connector part.

In one aspect the so-mated covers are unscrewed from the second part by engagement of the second conduit, e.g. the second end of the second conduit, with the mated covers, and rotational movement of the second conduit communicated to the mated covers.

In one aspect the first and second conduits are made moveable relative to each other by means of a construction of the second part and the second conduit by which the second conduit can move relative to the second part. For example the second part and the second conduit may comprise relatively moveable telescoping sleeves, the second conduit being the inner sleeve. In one embodiment, between such sleeves there is a seal e.g. an elastomeric washer, relative to which the sleeves may slide relative to each other, to isolate the interior of the enclosure within the second part from the outside environment. A construction of the second conduit and second part in the firm of two such sleeves can also facilitate the above-mentioned rotational movement of the conduit to unscrew the mated covers, in that the sleeves may be rotatable relative to each other, and the second conduit may be rotatable within the sleeve of the second part. Furthermore the above-mentioned telescoping movement of such sleeves facilitates the engagement of the second conduit with the mated covers by means of the second conduit being moveable by the telescoping movement into a position in which the second end of the second conduit engages with the mated covers, e.g. by means of a male-female engagement of the second end with a female socket on the part of the second cover which faces the interior of the second enclosure.

The second part may be provided with means to assist the detachment of the mated first and second covers from the second part. For example if, as in the above-described construction, the so-mated covers are unscrewed from the second part by engagement of the second conduit with the mated covers, and the second conduit is moveable relative to the second connector part, the second connector part may include one or more abutment part(s) against which the mated covers may abut, for example to displace them from the second conduit. If the second connector part comprises sleeves as described above, then an abutment part may be positioned such that relative longitudinal and/or rotational movement of the sleeves, e.g. of the second conduit within the outer sleeve of the second part, may cause the abutment part(s) to abut against the mated covers and the mated covers to fall off the second conduit into the enclosure within the second part.

When the second conduit and connector part comprise the sleeves described above and are capable of relative rotational and longitudinal motion, then the sleeves may have guide means to guide the sleeves in defined rotational and/or longitudinal motion., i.e. in defined directions and to defined distances. Such guide means may for example comprise one or more sets(s) of engaging finger(s) and guide track(s) e.g. a guide groove, which the guide finger follows. Such guide means can for example ensure that the sleeves can only rotate relative to each other to the extent necessary to unscrew the mated first and second covers from the second part.

The connector device of the invention may be provided with non-re-use connection means, e.g. snap fit connections to prevent the device from being disconnected and re-used. This can prevent re-use of the device and consequent contamination. For example such connections can be provided between the first and second parts to lock them together once engaged.

As a further safety feature the connector device of the invention may be provided with means to prevent the first and/or second covers from being separated from the respective first and second parts until the first and second parts have mated and established the second seal between them. For example if the connector device is constructed so that the second seal can be separated from the second part by a movement of the second conduit relative to the second connector part, the second conduit and the second connector part may have respective cooperating means to restrain the second conduit from moving relative to the second part, and these co-operating means may be disengaged upon mating of the first and second connector parts.

If the above-mentioned first and second connector parts, and/or first and second removable covers which mate together do so by means of co-operating screw threads then preferably non-return ratchet means are provided between these mating parts to prevent them from becoming unscrewed again. Such ratchet means are also advantageous when the above mentioned first removable cover mates with the first connector part by means of cooperating screw threads, and/or the second removable cover mates with the second connector part by means of co-operating screw threads, by preventing the mated first and second connector parts, and the mated first and second covers, from becoming un-mated when the mated first and second removable covers are detached from the mated first and second connector parts. Such unwanted un-matings could breach sterile seals between them and allow contamination.

The parts of the connector, e.g. the above mentioned first and second parts, covers etc., other than specifically elastomeric parts, may be made of robust plastics or metals, preferably of materials which can easily be sterilised, e.g. by heat, radiation etc. without suffering damage. Compression seals are suitably made of compressible elastomeric material such as synthetic or natural rubber.

It is an important feature of this invention that the first, second, third and fourth seals meet along a common seal line, and the mated first and second covers detach from the mated first and second parts at this common seal line. This seal line can define a single line of non-confidence between all the above mentioned parts of the connector which mate and separate, enabling a construction in which the interior of the connector can be maintained sterile without opportunity for micro-organisms to infiltrate into the region where the ends of the two conduits meet.

In one embodiment, this feature is achieved by the first seal between the first cover and the first part being provided by a first compression seal in the form of a ring shaped elastomeric washer having an outer rim in the shape of a ring shaped edge, e.g. of a bi-conical shape with both conical surfaces meeting at their base, and the third seal between the second removable cover and the opening also being provided by a second compression seal in the form of a ring shaped washer having an inward facing rim in the shape of an inward facing edge. In this construction the second seal between the first and second sealing surfaces is formed between the first seating surface and the second compression seal, and the fourth seal between the first and second covers is formed between the second cover and the first compression seal. In this embodiment, when the first and second parts are mated and the first and second covers are engaged the respective outward facing edge of the first compression seal and the inward facing edge of the second compression seal meet to define the common seal line. In this embodiment as the mated first and second covers detach from the mated first and second parts the outward facing edge of the first compression seal becomes separated from the inward facing edge of the second compression seal along this common seal line.

The invention will now be described by way of example only with reference to the accompanying Figures.

DETAILED DESCRIPTION

A seal which maintains the sterility of the interior of an enclosure bounded by the seal from entry of micro-orgianisms from the exterior of the seal is called herein a "sterile seal".

Parts referred to in FIGS. 1–12:
10 first connector part
11 screw thread
12 first sealing surface
13 first conduit
13A first open end of first conduit
13B second open end of first conduit
14 flexible plastics material tube
15 cylindrical body
16 first removable cover
17 screw thread connection
18 first seal, between the first cover 16 and the first part 10
19 compressible elastomeric washer
19A outer rim of washer 19
110 first enclosure
111 protective cap
112 screw thread
20 second connector part
21 screw thread
22 second sealing surface
23, 24 sub assemblies of second part 20
25 second enclosure
26 second compression seal
26A inward facing rim of seal 26
27 opening through second sealing surface 22
28 second removable cover
29 screw thread connection
210 third seal between cover 28 and compression seal 26

211 part of the second connector part 20 in the form of a cylindrical sleeve
212 second conduit
212A second open end of second conduit 212
212B opposite open end of second conduit 212
213 polygonal socket in cover 28
214 flexible plastics material tube
215 part of conduit 212 made into a cylindrical outer sleeve
215A part of sleeve 215 of larger diameter
216, 217 elastomeric seals
218 integral flange
219 guide finger
220 guide groove
221 protective cap
222 second seal between first and second sealing surfaces
223 screw thread
224 fourth seal between first and second covers
225 abutment surface of enclosure 25
226 arm
227 guide pin
228 guide groove
1234 common seal line
2201, 2202, 2203, 2204, 2205 five lengths of groove 220
30,31 non return ratchets and co-operating teeth
32 outer collar
33 ratchet springs
34 teeth
35 small sleeve
36 small sleeve NB: for clarity each feature is not numbered in every figure.

Figure 1:
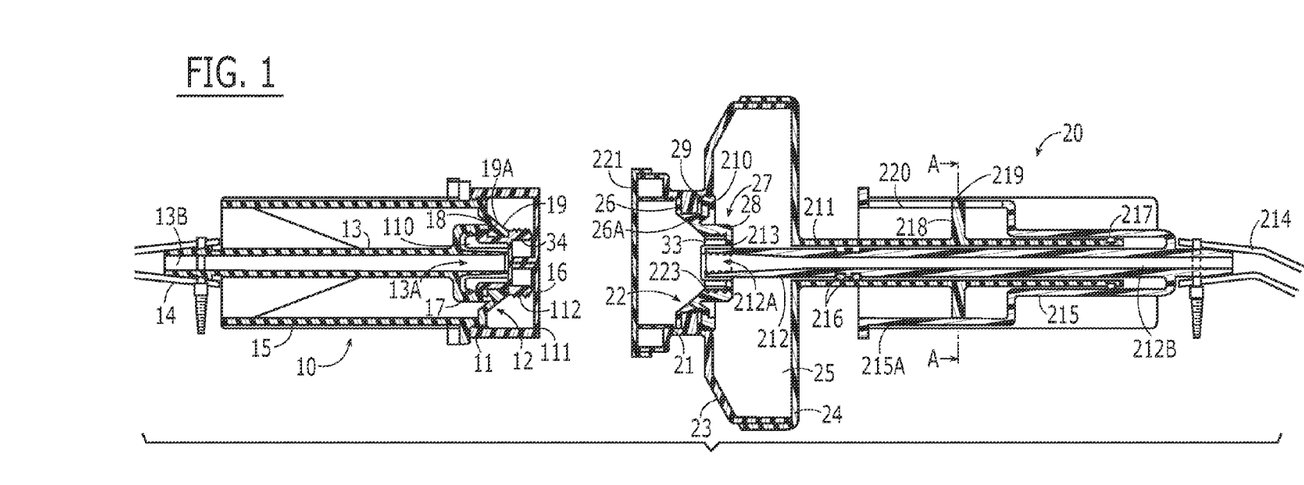
FIG. 1 shows one embodiment of the presently disclosed device in longitudinal view, and, as discussed in the description below, shows the device before the two parts are mated.

Referring to FIG. 1, a connector for connecting two conduits is shown. This comprises a first connector part 10 overall and a second connector part 20 overall. The first part 10 and second part 20 can be mated together by means of respective screw threads 11 and 21. The first part 10 and second part 20 have a respective first sealing surface 12 and a second sealing surface 22, which are respective flange surfaces. Parts 10 and 20 are made of robust plastics material.

Through the first part 10 passes a first conduit 13 having a first open end 13A on one side of the sealing surface 12, viz., the side that faces part 20 during assembly as described below. The first conduit 13 is a tubular conduit and has a second open end 13B on the other side of the sealing surface 12, which can be connected to another tube, e.g. a flexible plastics material tube 14. The first part 10 is overall in the form of a cylindrical body 15, with the first sealing surface 12 forming a closed end wall of the body 15.

Covering the open end 13A of the conduit 13 is a first removable cover 16. This is engageable with the first connector part 10 by means of a screw thread connection 17. When engaged with first part 10 the cover 16 forms a first seal 18 between the first cover 16 and the first part 10, provided by a compression seal being a compressible elastomeric washer 19 between the first cover 16 and the first part 10, and this is a sterile seal. Washer 19 is in the shape of a ring shaped washer having an outer rim 19A in the shape of a ring shaped edge, and is generally of a bi-truncated conical shape with both conical surfaces meeting at their base, i.e. edge 19A. The first connector part 10 and the cover 16 form a first enclosure 110 enclosing the first open end. The seal 18 is a sterile seal isolating this enclosure 110 from the outside environment. Prior to use the cover 16 and surface 12 of the first part 10 may be protected by cap 111. The part of the first connector part 10 adjacent to the open end 13A of the first conduit is formed into a concavity, and the facing surface of first cover 16 is also concave to define between them the first enclosure 110.

Second connector part 20 is in the form of sub-assemblies 23 and 24 for ease of manufacturing and which fit sealingly together. Part 20 defines a second enclosure 25, and the sub-assemblies 23, 24 comprise body parts of the second part 20 forming surrounding walls of the second enclosure 25.

Second sealing surface 22 partly comprises a second compression seal 26 in the form of a ring shaped washer having an inward facing rim 26A in the form of an inward facing edge. When the first part and second part 20 are mated, as will be seen below, this second compression seal 26 forms a second seal between the first sealing surface 12 and the second sealing surface 22.

There is an opening 27 into second enclosure 25 through the second sealing surface 22, and there is a second removable cover 28, which is engageable with the second connector part 20 by means of screw thread connection 29 to thereby close the opening 27. The second enclosure 25 is thereby formed in part by the body parts 23,24 and the second removable cover 28. The second removable cover 28 is configured to connect with part 23 from the direction of the interior of enclosure 25. When in place as shown in FIG. 1 cover 28 closes opening 27 and a third seal 210 is formed between the cover 28 and the compression seal 26. A part 211 of the second connector part 20 is integrally in the form of a cylindrical sleeve extending longitudinally away from the opening 27, and open into the enclosure 25.

A second conduit 212 passes internally along sleeve 211 into enclosure 25, and terminates in a second open end 212A within the second enclosure. Conduit 212 is a cylindrical rigid tube which can rotate within sleeve 211, and end 212A of conduit 212 is engageable with cover 28, e.g. by means of the end 212A being polygonal and fitting in a male-female manner into a matching polygonal socket 213 in cover 28, or by means of mating splines on the cover 28 and end 212, so that rotation of conduit 212 when engaged with cover 28 may be communicated to cover 28, but the end 212A may be freely longitudinally inserted into and withdrawn from the socket 213 in cover 28. The socket 213 has a closed end facing the first part 10, and covers the end 212A of conduit 212. Conduit 12 has an opposite open 212B which can be connected to another flexible tube 214.

Part 215 of conduit 212 is integrally made into a cylindrical outer sleeve within which sleeve 211 closely fits and can freely rotate. Elastomeric seals 216 and 217 between respectively sleeve 211 and 212, and between sleeve 211 and 215 are sterile seals which isolate enclosure 25 from the environment.

Sleeve 211 is provided with an internal flange 218 in which part of the outer edge of which is a guide finger 219. Part 215A of outer sleeve 215 is made of increased diameter and there is a co-operating guide groove 220 in sleeve 215, to guide the parts of the connector along defined paths, as will be explained below with reference to FIG. 9. The opening 27 may be covered prior to use by protective cap 221.

The operation of the device of FIG. 1 will now be described with reference to FIGS. 2–10.

Figure 2:
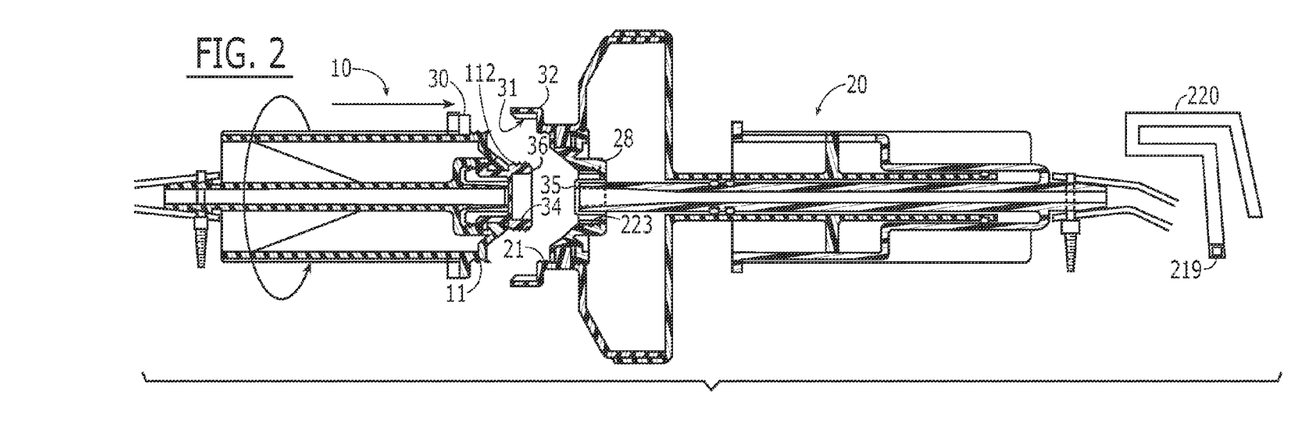
FIG. 2 shows one embodiment of the presently disclosed device in longitudinal view and, as discussed in the description below, shows the device before the two parts are mated. Immediately to the right of the longitudinal view is a surface schematic view of the guide groove 220 and guide finger 219.

As seen in FIG. 2 the caps 111 and 221 have been removed and parts 10 and 20 are brought toward each other so that screw threads 11, 21 on respectively first part 10 and second part 20 can engage by means of the rotation of part 10 relative to part 20 indicated by the arrow in FIG. 2. As will be explained later by reference to FIG. 10 a ratchet mechanism 30 31 co-operating between parts 10 and 20 permits relative rotation in the direction necessary to mate the screw threads 11, 21, but does not allow relative rotation in the opposite direction to unscrew them, and similarly a ratchet spring and teeth mechanism 33, 34 between the covers 16, 28 permits relative rotation in the direction necessary to mate the screw threads 112, 223 but does not allow relative rotation in the opposite direction to unscrew them.

Figure 3:
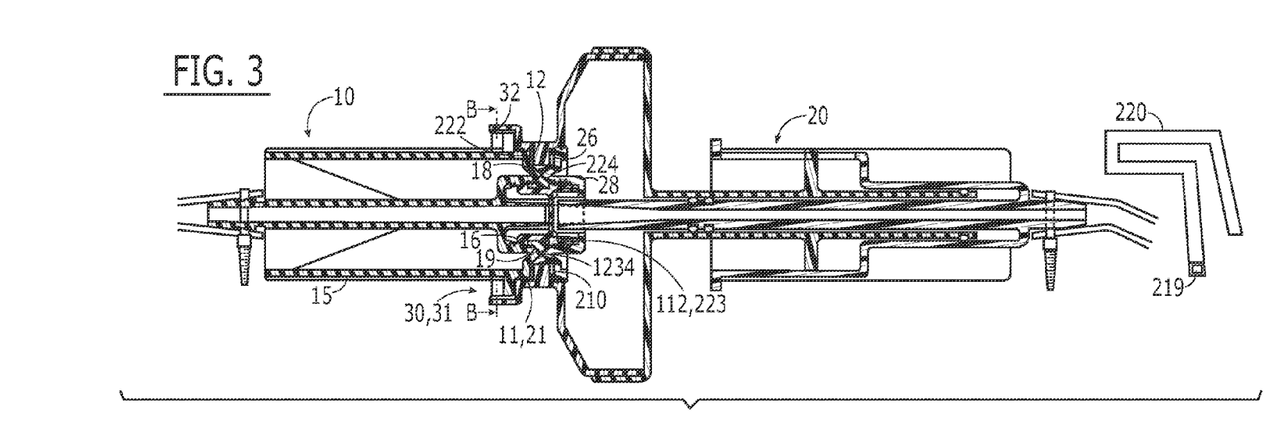
FIG. 3 shows one embodiment of the presently disclosed device in longitudinal view and, as discussed in the description below, shows one phase of its operation in which the two parts are mated. Immediately to the right of the longitudinal view is a surface schematic view of the guide groove 220 and guide finger 219.

As seen in FIG. 3 first part 10 and second part 20 have mated via respective screw threads 11, 21. A second seal 222 has been formed between the sealing surface 12 of the first part 10, and the sealing surface 22 of the second part 20, in which the compression seal 26 is compressed between these surfaces 12,22. This seal 222 is a sterile seal, preventing passage of micro-organisms from the outside environment. The mating of the first 10 and second 20 parts by engagement of screw threads 11, 21 also causes the first 16 and second 28 covers to mate, by means of respective screw threads 112, 223 to form a fourth seal 224 between the first 16 and second cover 28, that is, between cover 28 and first compression seal 19. The pitch of the screw threads 11, 21 and 112, 223 is such that when parts 10 and 20 are screwed tight, i.e. to their fullest extent, covers 16 and 28 are also screwed tight, i.e. to their fullest extent. When mated in this way, the mated first 16 and second 28 covers between them enclose all those parts of the first 16 and second 28 covers that before mating were exposed to the ambient environment. Therefore any micro-organisms etc. that may have contaminated the outer surface of covers 16, 28 are now sealed between covers 16 and 28. As seen in FIG. 3 the first 18, second 222, third 210 and fourth 224 seals all meet along a common seal line 1234, being the line along which the edges of the respectively inwardly and outwardly facing bi-conical surfaces of the rims 19A and 26A meet.

Figure 4:
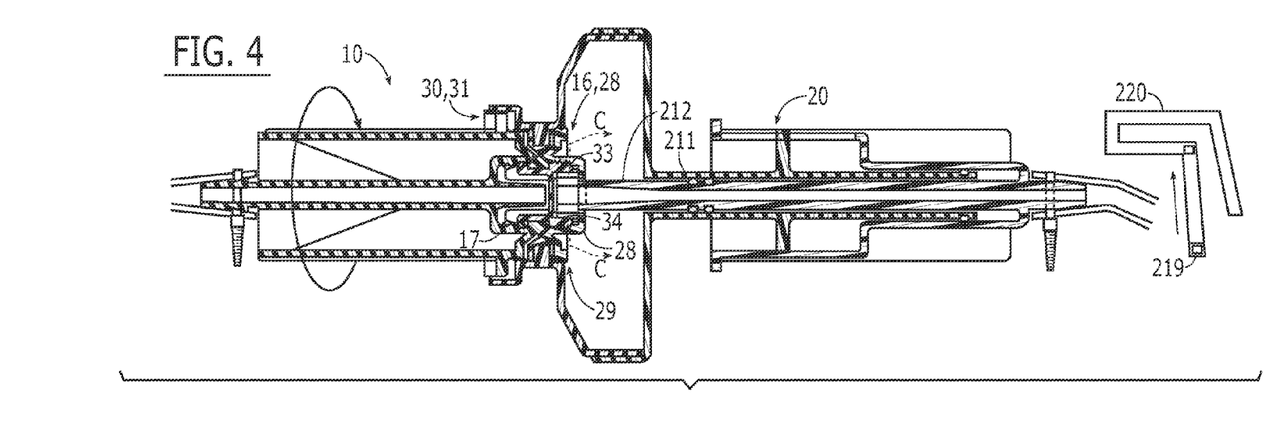
FIG. 4 shows one embodiment of the presently disclosed device in longitudinal view and, as discussed in the description below, shows one phase of its operation in which the two parts are mated. Immediately to the right of the longitudinal view is a surface schematic view of the guide groove 220 and guide finger 219.

As seen in FIG. 4, mated parts 10, 20 are now rotated relative to each other, in the direction indicated by the arrow, relative to conduit 212, which can freely rotate within sleeve part 211 of part 20. Ratchet parts 30, 31 and 33, 34 prevent the mated parts 10, 20 and 16,28 from becoming unscrewed as described above. This relative rotation is also communicated to second cover 28, which causes the mated covers 16, 28 to rotate relative to parts 10,20 and causes the mated covers 16,28 to become unscrewed at screw thread connection 17, 29 from parts 10,20.

Figure 5:
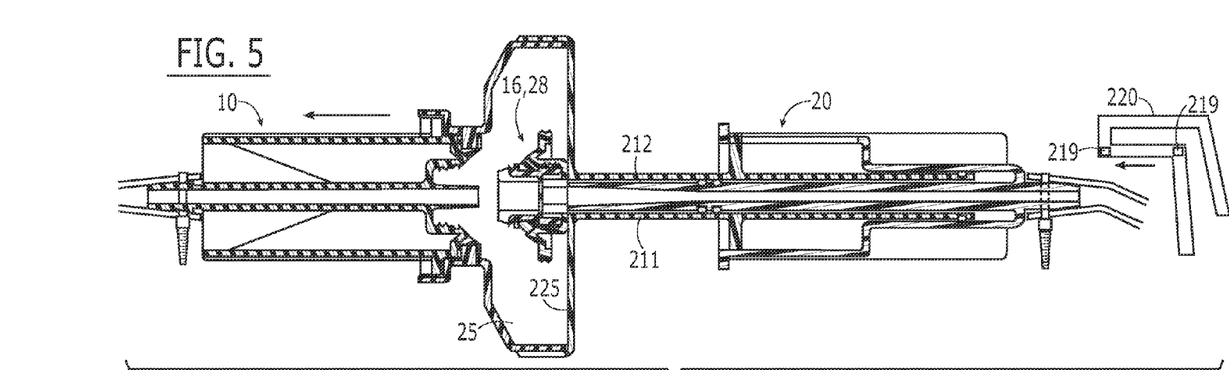
FIG. 5 shows one embodiment of the presently disclosed device in longitudinal view and, as discussed in the description below, shows one phase of its operation in which the two parts are mated. Immediately to the right of the longitudinal view is a surface schematic view of the guide groove 220 and guide finger 219.
Figure 6:
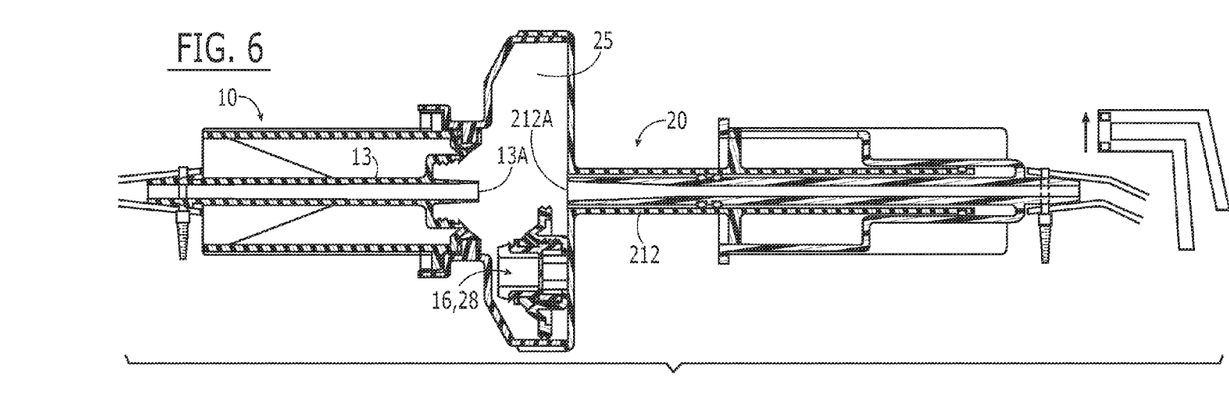
FIG. 6 shows one embodiment of the presently disclosed device in longitudinal view and, as discussed in the description below, shows one phase of its operation in which the two parts are mated. Immediately to the right of the longitudinal view is a surface schematic view of the guide groove 220 and guide finger 219.

As seen in FIGS. 5 and 6, the unscrewing of the mated first 16 and second 28 covers results in these mated covers 16,28 becoming detached from the mated first 10 and second 20 parts. The conduit 212 can move longitudinally within sleeve 211 away from opening 27, and this longitudinal movement of the conduit 212 relative to sleeve 211 causes the mated covers 16,28 to first become distanced from the end 13A of conduit 13, then to abut against abutment surface 225 of enclosure 25 i.e. the wall of the enclosure 25 opposite to opening 27.

As seen in FIG. 6 this causes the mated covers 16,28 to fall clear of end 212A of conduit 212, consequently exposing the first 13A and second 212A ends respectively of the first 13 and second 212 conduits to each other within enclosure 25. The mated covers 16,28 are received within enclosure 25 which is of such shape and dimensions that the received mated covers 16,28 do not interfere with further operation of the device.

Figure 7:
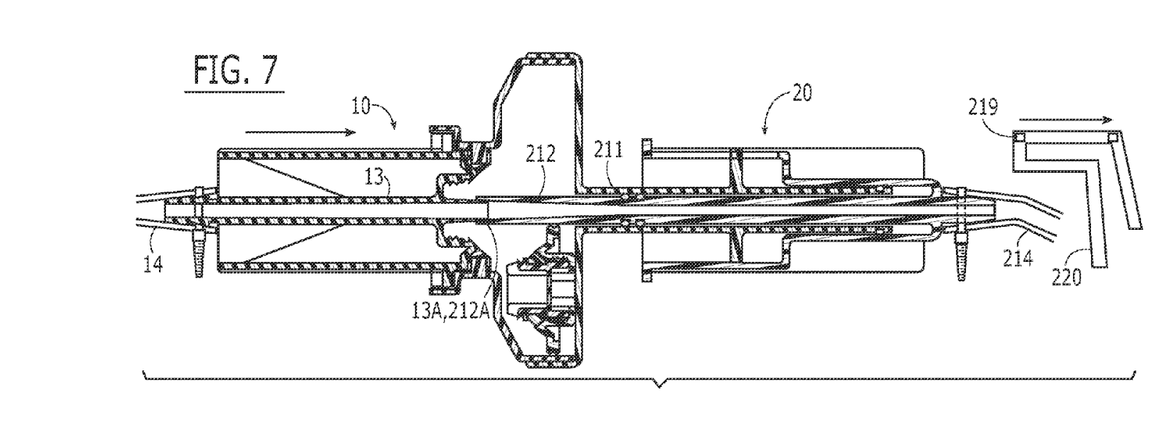
FIG. 7 shows one embodiment of the presently disclosed device in longitudinal view and, as discussed in the description below, shows one phase of its operation in which the two parts are mated. Immediately to the right of the longitudinal view is a surface schematic view of the guide groove 220 and guide finger 219.
Figure 8:
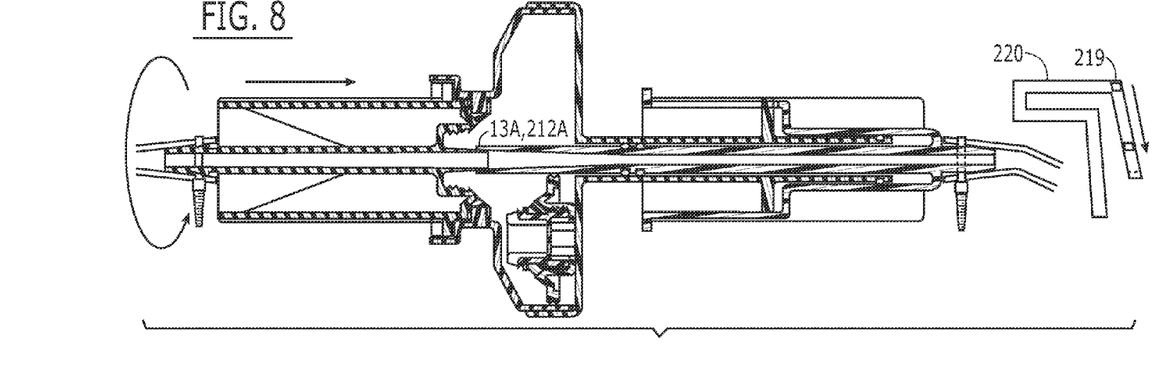
FIG. 8 shows one embodiment of the presently disclosed device in longitudinal view and, as discussed in the description below, shows one phase of its operation in which the two parts are mated. Immediately to the right of the longitudinal view is a surface schematic view of the guide groove 220 and guide finger 219.
Figure 9:
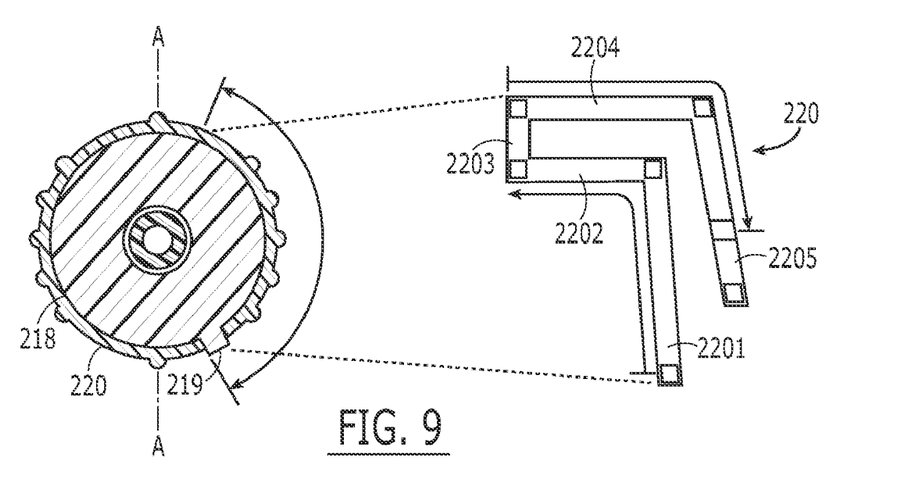
FIG. 9 shows a cross section of one embodiment of the presently disclosed device, as discussed in the description below. Immediately to the right of the longitudinal view is a surface schematic view of the guide groove 220 and guide finger 219.

As seen in FIGS. 7 and 8 the conduit 212 has been slid within outer sleeve 211 toward end 13A of conduit 13, and the first 13A and second 212A ends of the first 13 and second 212 conduits have come into communication. The ends 13A and 212A are mating male-female connections and further relative rotation as shown in FIG. 8 caused them to form a fluid tight fit, and furthermore the finger 219 moves into its final locking position in groove 220. Fluid can then flow from tube 14 through the mated connector 10, 20 to tube 214 and vice versa. The ends 13A and 212A may co-operate as shown by means of a frictional engagement, or they may have connection means (not shown), e.g. engaging screw threads or bayonet connections etc., and they may be provided with further seals (not shown) to facilitate their fluid tight connection.

As seen in FIG. 3, when the first 10 and second 20 parts are mated as described above, the first 18, second 222, third 210 and fourth 224 seals all meet along a common seal line 1234, being the line along which the rims 19A and 26A meet. The mated first 16 and second 28 covers detach from the mated first 10 and second 20 parts at this common seal line 1234. This means that all those parts of the connector which prior to mating of the first 10 and second 20 parts were exposed to the ambient environment can be separated from all the sterile parts of the connector across this line 1234, which establishes a line of non-confidence.

In use, the parts 10 and 20 may be provided in a sterile pack (not shown) e.g. a sealed plastic bag. The conduits 13 and 212 may be connected to respective tubes 14 and 214 in separate sterile environments, and tubes 14 and 214 may themselves be connected to respective sterile containers containing respective sterile fluids (not shown). The containers with connected tubes 14, 214 and connected parts 10,20 may then be transported through a non-sterile environment and connected as described above so that sterile fluid may flow between them without contamination of the fluid by micro-organisms in the ambient environment.

Figure 10A:
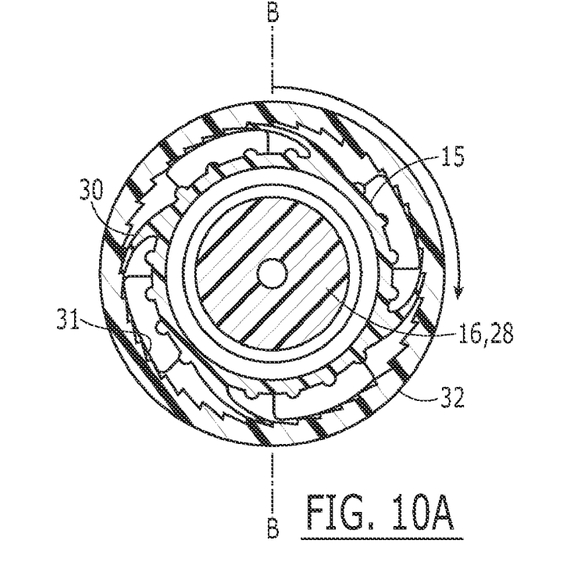
FIG. 10A shows one embodiment of the presently disclosed device in cross section, as discussed in the description below.
Figure 10B:
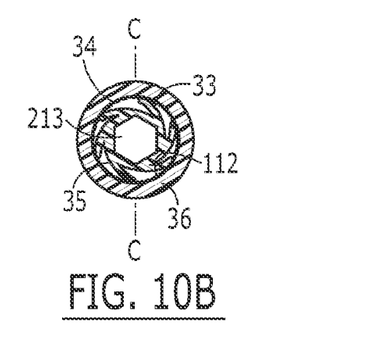
FIG. 10B shows one embodiment of the presently disclosed device in cross section, as discussed in the description below.
Figure 10C:
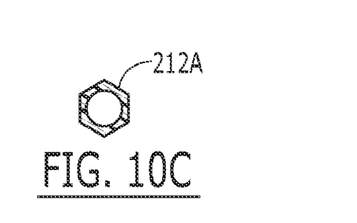
FIG. 10C shows one embodiment of the presently disclosed device in cross section, as discussed in the description below.

FIG. 10 shows cross sections through the mated parts 10, 20 as shown in FIG. 3 at lines B—B and also through the mated first and second covers 16, at lines C—C in FIG. 4, looking in the direction indicated by the arrows, and shows non-return ratchet springs 30 and co-operating teeth 31 integrally respectively on part 15 and an outer collar 32 of part 20 to prevent the parts 10, 20 from becoming disconnected during use. FIG. 10 also shows co-operating non-return ratchet springs 33 and teeth 34 on respectively the first removable cover 16 and second removable cover 28, to prevent disconnection of the covers 16,28 accidentally. The ratchet springs 33 are integrally formed on the outer surface of a small sleeve 35 which surrounds the polygonal socket 213 in cover 28, and the teeth 34 are integrally formed on the inner surface of the small sleeve 36, on the outer surface of which is the screw thread 112.

FIG. 10 also shows the polygonal shape of the end 212A of conduit 212 and the socket 213 in second cover 28.

Figure 11:
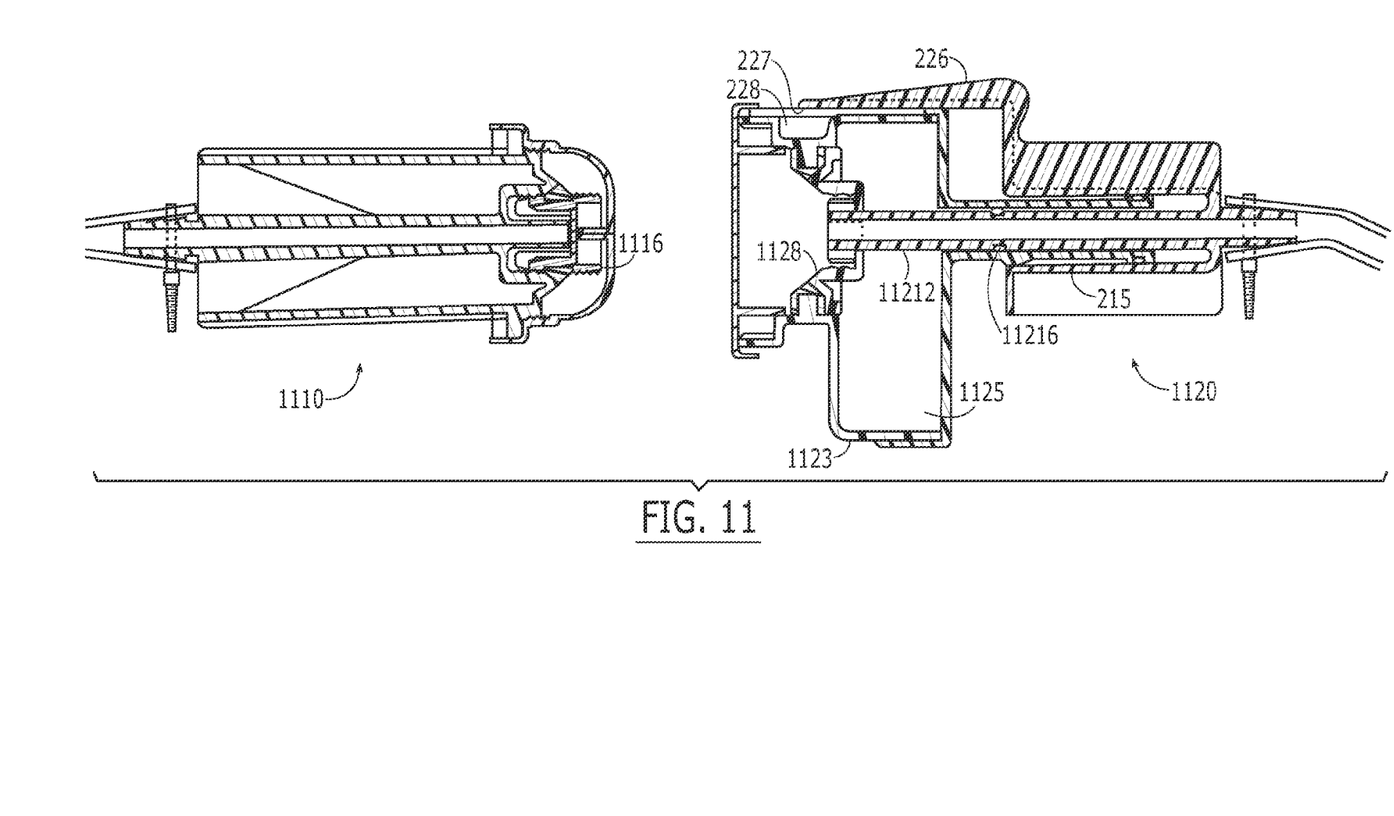
FIG. 11 shows another embodiment of the presently disclosed connector device.

Referring to FIG. 11 another embodiment of the connector device is shown. It will be apparent that the overall construction and operation of the device shown in FIG. 11 is analogous to that of FIGS. 1–10, i.e. comprising the two parts 1110 and 1120. The device of FIG. 11 differs from FIGS. 1–10 in that the second conduit 11212 has been made ergonomically shorter than the conduit 212 of FIGS. 1–10, and a single seal 11216 is used. Also the enclosure 1125 has been made oval in section as cut across the length direction of the conduit 11212 with the conduit in the upper half of the oval to provide more space to receive the mated first and second covers 1116, 1128. Also the guide finger 219 and guide groove 220 are replaced by an arm 226 extending from sleeve 215 and terminating in a guide pin 227 which can follow a guide groove 228 in the outer surface of the part 1123 in a manner analogous to the pin 219 and groove 220 of FIGS. 1–10. Also as a safety feature to prevent premature operation of the part 1120 i.e. separation of the cover 1128 from part 1123, the pin 227 may be initially locked immovably in place in groove 228 and unable to move therein, and the pin 227 may be released from this locked position only when parts 1110 and 1120 mate. This may be achieved by a resilient biasing of the pin into a locked position e.g. by the arm 226 being resilient, and by for example a cam surface (not shown) on part 1120 which engages a cam surface (not shown) acting on the pin 227 when parts 1110 and 1120 mate to thereby urge the pin 227 out of this locked position into an unlocked position in which it can move in groove 228 and allow operation of the connector device as described above.

FIG. 12 shows the construction and operation of an embodiment of the presently disclosed connector more schematically, clarifying the principle of the embodiments of FIGS. 1 to 11.

Figure 12A:
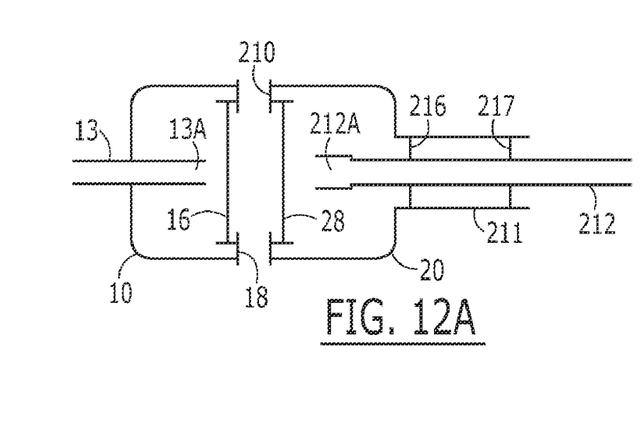
FIG. 12A-12D show an embodiment of the presently connector device more simply and schematically.

The connector comprises a first connector part 10 and a second connector part 20, which can mate together to form an enclosure 25 between them bounded by a sterile seal but which in FIG. 12A are shown un-mated but adjacent. The first connector part 10 and second connector part 20 have respective first and second conduits 13,212 passing through them. The second conduit 212 is slideably relative to second connector part 20 within the sleeve 211, sterile sliding seals 216,217 being provided to maintain sterility. In this unmated state of the first and second connector parts 10,20 the ends 13A, 212A of the first and second conduits 13,212 are covered by respective first and second removable covers 16,28 which can mate with each other and which form respective seals 18,210 with the respective first and second connector parts 10,20 to isolate the ends 13A,212A of the conduits 13,212 from the ambient environment.

Figure 12B:
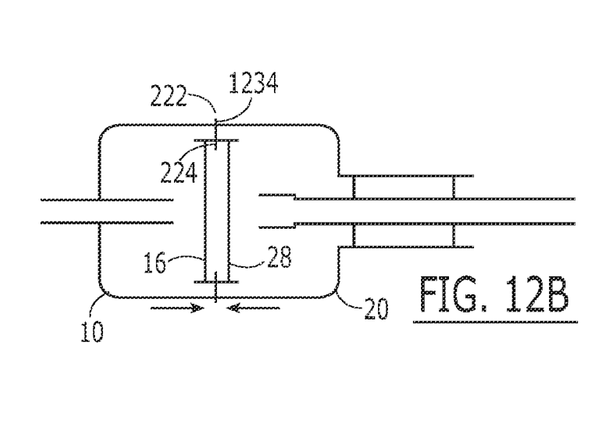

In FIG. 12B the parts 10,20 are shown mated by a relative translation movement as shown by the arrows. A sterile seal 222 has formed between the first and second parts, and the first and second removable covers 16,28 have also mated with each other and formed a sterile seal 224 with each other. In this configuration the seals between the first and second parts 10,20, between the respective first and second movable covers 16,28 and the parts 10,20 all meet at a common seal line 1234.

Figure 12C:
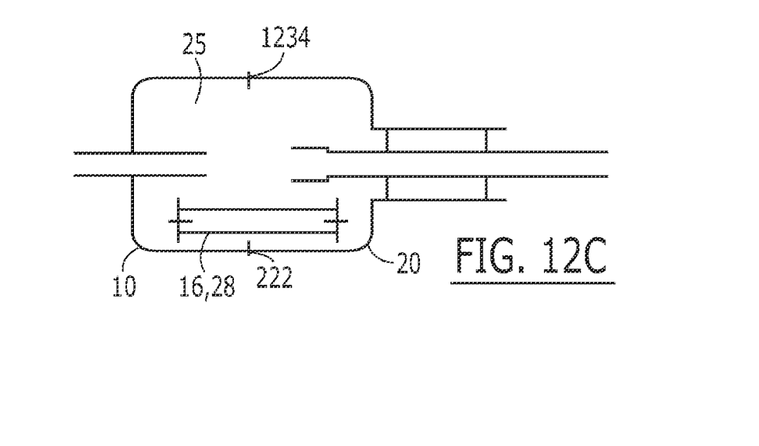

In the mated configuration shown in FIG. 12C, the mated first and second covers 16,28 have become separated from the respective first and second parts 10,20 and received within the enclosure 25. The common seal line 1234 is the line at which the mated first and second removable covers 16,28 are separated from the respective first and second parts 10,20.

Figure 12D:
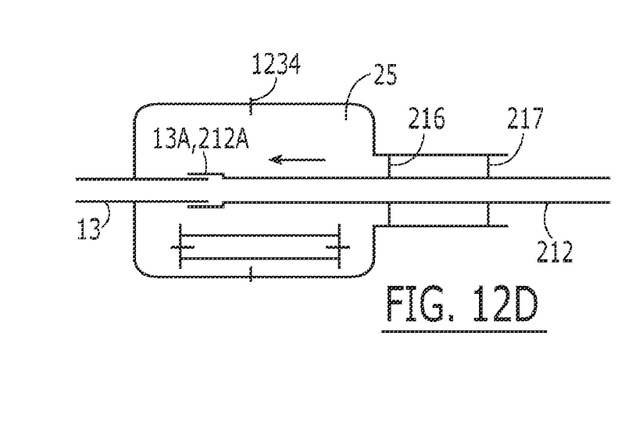

As shown in FIG. 12D the second conduit 212 is moved relative to the first conduit 13 and comes into mating connection with the first conduit 13 within the enclosure 25, the seals 216,217 maintaining the enclosure 25 sterile.

The invention claimed is:

1. A connector for connecting two conduits which comprises, a first connector part and a second connector part which mate together to form an enclosure between them bounded by a sterile seal, the first connector part and second connector part having respective first and second conduits passing through them, the conduits being relatively moveable within the enclosure formed on mating of the first and second connector parts to form a mating connection between the first and second conduits, in the unmated state of the first and second connector parts the first and second conduits being covered by respective first and second removable covers which can mate with each other and form a sterile seal between them, and which form respective seals with the respective first and second connector parts to isolate the ends of the conduits from the ambient environment, wherein in operation, on mating of the first and second connector parts the first and second removable covers also mate, then the mated covers are detached from the mated respective first and second parts and are received within the enclosure, to thereby expose the respective first and second ends of the first and second conduits to each other within the enclosure, and to allow the conduits to relatively move and come into mating connection within the enclosure.

2. A connector according to claim 1 wherein there is a sterile seal between the first connector part and first removable cover; a sterile seal between the second connector part and second removable cover; a sterile seal between the first connector part and second connector part when mated; and a sterile seal between the first removable cover and the second removable cover when mated, and all of these seals meet at a common seal line.

3. A connector according to claim 1 wherein, a first connector part having a first sealing surface through which passes a first conduit having a first open end on one side of the sealing surface, a first removable cover engageable with the first connector part and which when so engaged forms a first seal between the first cover and the first part, and together with the first connector part forms a first enclosure enclosing the first open end, a second connector part defining at least part of a second enclosure, and having a second sealing surface which can be sealingly mated with the first sealing surface to form a second seal between these surfaces, an opening through the second sealing surface, a second removable cover engageable with the second connector part which when in place closes the opening at a third seal, and which together with the second connector part forms a second enclosure within the second connector part, and the second removable cover can mate with the first removable cover, a second conduit terminating in a second open end within the second enclosure and having an open end outside the second enclosure, wherein in operation the first and second parts mate to form the second seal between the first and second sealing surfaces, when so mated the first and second covers mate to form a fourth seal between the first and second covers, and the mated first and second covers enclose between them parts of the first and second covers that before mating were exposed to the ambient environment, the mated first and second covers are detached from the mated first and second parts to expose the first and second ends respectively of the first and second conduits to each other, the first and second ends respectively of the first and second conduits are moveable relatively toward each other, and are moved relative to each other into communication, and wherein, the first, second, third and fourth seals meet along a common seal line, and the mated first and second covers detach from the mated first and second parts at this seal line.

4. A connector according to claim 3 wherein the first and second conduits are tubes, and the respective first and second ends are mating ends which can mate to form a fluid-tight communication.

5. A connector according to claim 3 wherein the first part and first cover have co-operating screw threads to facilitate the sealing of the cover against the first part, the second removable cover and the opening through the second connector part have screw threads to facilitate the sealing of the cover against the second part to seal the opening, and the first and second covers have co-operating screw threads to facilitate their mating together.

6. A connector according to claim 3, wherein the second removable cover is detachable from the second connector part by a movement inwardly into the second enclosure.

7. A connector according to claim 1 wherein the mated first and second covers are detachable from the mated first and second parts by unscrewing of the second cover from the second part, and the so-mated covers can be unscrewed from the second part by engagement of the second conduit with the mated covers and rotational movement of the second conduit is communicated to the mated covers.

8. A connector according to claim 7 wherein when engaged with the second conduit the mated first and second covers may be carried by the second conduit away from the opening.

9. A connector according to claim 1 wherein the second connector part and the second conduit comprise relatively moveable telescoping sleeves whereby the second conduit may be moved relative to the second part away from the opening.

10. A connector according to claim 7, wherein the second connector part includes one or more abutment part(s) against which the mated first and second covers may abut to displace them from the second conduit.

11. A connector according to claim 1 wherein the detached mated covers are received within the second connector part.

12. A connector according to claim 9 wherein the sleeves have guide means to guide the sleeves in defined rotational and/or longitudinal motion.

13. A connector according to claim 1 wherein non-re-use connection means prevent the first and second connector parts from being disconnected and re-used.

14. A connector according to claim 13 wherein the first and second connector parts, and/or first and second removable covers which mate together do so by means of co-operating screw threads and said non-re-use connection means comprise non-return ratchet means.

15. A connector according to claim 2 wherein the common seal line defines a single line of non-confidence between all the parts of the connector which mate and separate.

16. A connector according to claim 15 wherein the first seal between the first cover and the first part is provided by a first compression seal in the form of a ring shaped elastomeric washer having an outer rim in the shape of a ring shaped edge, the third seal between the second removable cover and the opening also being provided by a second compression seal in the form of a ring shaped washer having an inward facing rim in the shape of an inward facing edge, the second seal between the first and second sealing surfaces is formed between the first sealing surface and the second compression seal, and the fourth seal between the first and second covers is formed between the second cover and the first compression seal.

17. A connector according to claim 16 wherein when the first and second parts are mated and the first and second covers are mated the respective outward facing edge of the first compression seal and the inward facing edge of the second compression seal meet to define the common seal line, and as the mated first and second covers detach from the mated first and second parts the outward facing edge of the first compression seal becomes separated from the inward facing edge of the second compression seal along this common seal line.

18. A connector according to claim 1, with means to prevent the first and/or second covers from being separated from the respective first and second parts until the first and second parts have mated and the second seal is established between them.

* * * * *